(12) United States Patent
Twomey et al.

(10) Patent No.: US 9,113,909 B2
(45) Date of Patent: Aug. 25, 2015

(54) SURGICAL VESSEL SEALER AND DIVIDER

(75) Inventors: John R. Twomey, Longmont, CO (US); Monte S. Fry, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1003 days.

(21) Appl. No.: 13/223,521

(22) Filed: Sep. 1, 2011

(65) Prior Publication Data
US 2013/0060250 A1 Mar. 7, 2013

(51) Int. Cl.
*A61B 18/14* (2006.01)
*A61B 17/00* (2006.01)
*A61B 17/29* (2006.01)

(52) U.S. Cl.
CPC ... *A61B 18/1447* (2013.01); *A61B 2017/00734* (2013.01); *A61B 2017/2902* (2013.01); *A61B 2017/2937* (2013.01); *A61B 2018/1455* (2013.01)

(58) Field of Classification Search
CPC ....... A61B 17/29; A61B 17/295; A61B 18/14
USPC .......................................... 606/52, 206, 171
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Alyssa M Alter

(57) ABSTRACT

A forceps includes an end effector assembly having first and second jaw members. Each jaw member includes an elongated proximal segment and a distal segment. The distal segments are configured to grasp tissue therebetween. The jaw members are biased towards a spaced-apart position relative to one another. A sliding unit is disposed about the first and second jaw members and is slidable relative to the jaw members between a first position, wherein the sliding unit is disposed about the elongated proximal segments of the jaw members, and a second position, wherein the sliding unit is disposed about the distal segments of the jaw members. The sliding unit is configured to transition the jaw members against the bias from the spaced-apart position to an approximated position for grasping tissue therebetween upon sliding of the sliding unit from the first position to the second position.

16 Claims, 10 Drawing Sheets

(56) References Cited

U.S. PATENT DOCUMENTS

| | | | |
|---|---|---|---|
| 5,797,958 A | 8/1998 | Yoon | |
| D402,028 S | 12/1998 | Grimm et al. | |
| D408,018 S | 4/1999 | McNaughton | |
| D416,089 S | 11/1999 | Barton et al. | |
| 5,984,939 A * | 11/1999 | Yoon | 606/170 |
| 5,993,466 A * | 11/1999 | Yoon | 606/147 |
| D424,694 S | 5/2000 | Tetzlaff et al. | |
| D425,201 S | 5/2000 | Tetzlaff et al. | |
| 6,074,389 A * | 6/2000 | Levine et al. | 606/45 |
| H1904 H | 10/2000 | Yates et al. | |
| 6,273,887 B1 | 8/2001 | Yamauchi et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,419,640 B1 * | 7/2002 | Taylor | 600/564 |
| 6,419,675 B1 | 7/2002 | Gallo, Sr. | |
| 6,464,702 B2 | 10/2002 | Schulze et al. | |
| D465,281 S | 11/2002 | Lang | |
| D466,209 S | 11/2002 | Bon | |
| 6,652,521 B2 | 11/2003 | Schulze | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| 7,011,657 B2 | 3/2006 | Truckai et al. | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.

(56) References Cited

OTHER PUBLICATIONS

U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et aI, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.

(56) References Cited

OTHER PUBLICATIONS

Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL VESSEL SEALER AND DIVIDER

BACKGROUND

The present disclosure relates to surgical instruments and, more particularly, to surgical forceps for grasping, sealing, and/or dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

An endoscopic surgical forceps typically includes an elongated shaft having an end effector assembly, e.g., a pair of jaw members, disposed at the distal end thereof. The elongated shaft permits the surgeon to insert the end effector assembly through a relatively small access opening in the body to the internal surgical site, while the remainder of the endoscopic forceps remains disposed externally of the surgical site. The surgeon may then control the operation of the end effector assembly, e.g., to grasp, seal, and/or divide tissue, by manipulating the proximal end of the forceps.

SUMMARY

In accordance with one embodiment of the present disclosure, a forceps is provided. The forceps includes an end effector assembly having first and second jaw members. Each jaw member including an elongated proximal segment and a distal segment. The distal segments of the jaw members are configured to grasp tissue therebetween and are biased towards a spaced-apart position relative to one another. A sliding unit is disposed about the first and second jaw members and is slidable relative thereto between a first position, wherein the sliding unit is disposed about the elongated proximal segments of the jaw members, and a second position, wherein the sliding unit is disposed about the distal segments of the jaw members. The sliding unit is configured to transition the jaw members against the bias from the spaced-apart position to an approximated position for grasping tissue therebetween upon sliding of the sliding unit from the first position to the second position.

In one embodiment, a plunger is coupled to the sliding unit and is configured for movement relative to the jaw members between a proximal position and a distal position for sliding the sliding unit between the first and second positions. The plunger may further include a knob disposed at a proximal end thereof that is configured to facilitate translation of the plunger between the proximal and distal positions.

In another embodiment, a housing is provided. The housing is configured to engage the first and second jaw members therein. Further, the housing may include first and second handles extending outwardly therefrom that are configured to facilitate grasping of the housing.

In another embodiment, the plunger is selectively translatable relative to the housing between the proximal position, wherein the plunger substantially extends proximally from the housing, and the distal position, wherein the plunger is substantially disposed within the housing.

In yet another embodiment, the forceps further includes a shaft extending distally from the housing. The shaft is engaged to the plunger at a proximal end thereof such that movement of the plunger between proximal and distal positions effects similar movement of the shaft between a proximal position and a distal position. The shaft is also engaged to the sliding unit at a distal end thereof such that movement of the shaft between the proximal and distal positions slides the sliding unit relative to the jaw members between the first and second positions.

In still another embodiment, the proximal segment of each of the jaw members extends proximally through a lumen defined within the shaft and into the housing. As mentioned above the proximal segments of the jaw members may be engaged within the housing at the proximal ends thereof.

In still yet another embodiment, each of the jaw members includes an opposed tissue sealing plate disposed on the distal segment thereof. The tissue sealing plates are configured to grasp tissue therebetween upon transitioning of the jaw members to the approximated position.

The tissue sealing plates may be formed from an electrically-conductive material. In such an embodiment, the tissue sealing plates are adapted to conduct electrical energy therebetween for sealing tissue grasped therebetween. Further, the jaw members may also be formed from an electrically-conductive material to transmit electrosurgical energy from a proximal end thereof to the tissue sealing plates disposed thereon at the distal ends thereof.

In another embodiment, the sliding unit is formed from an insulative material.

In another embodiment, a knife is engaged within the sliding unit. The knife is configured to cut tissue grasped between the jaw members upon sliding of the sliding unit from the first position to the second position. Further, one or both of the jaw members may include a knife channel extending longitudinally therethrough. The knife channel(s) is configured to permit reciprocation of the knife therethrough as the sliding unit is slid between the first and second positions.

In still another embodiment, the sliding unit includes first and second tracks defined therein. Each track is configured to slidably receive one of the jaw members therein to guide the sliding unit along the jaw members as the sliding unit is slid between the first and second positions.

In yet another embodiment, each of the tracks further includes a jaw member track portion and a sealing plate track portion. The jaw member track portions are configured to receive the jaw members therein, while the sealing plate track portions are configured to receive the tissue sealing plates of the jaw member therein as the sliding unit is slid from the first position to the second position.

In still yet another embodiment, each of the jaw members further includes an intermediate segment interconnecting the proximal and distal segments thereof. The intermediate segment of one or both of the jaw members includes a biasing member configured to bias the jaw members towards the spaced-apart position. For example, the intermediate segment(s) may include a flat spring.

BRIEF DESCRIPTION OF THE DRAWINGS

Various embodiments of the present disclosure are described herein with reference to the drawings wherein.

DETAILED DESCRIPTION

Figure 1:
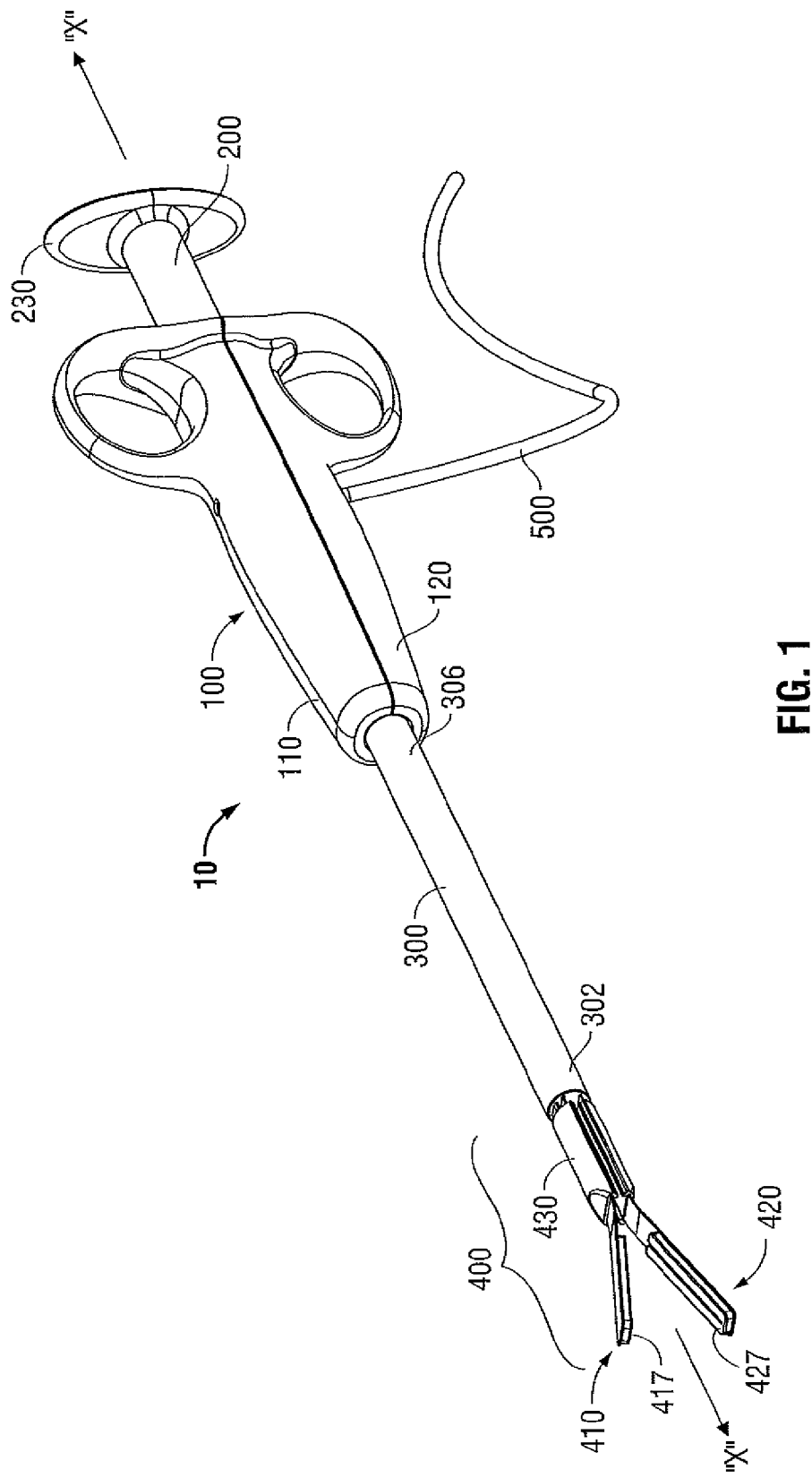
FIG. 1 is a side, perspective view of one embodiment of a forceps provided in accordance with the present disclosure, wherein jaw members of the forceps are disposed in a spaced-apart position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
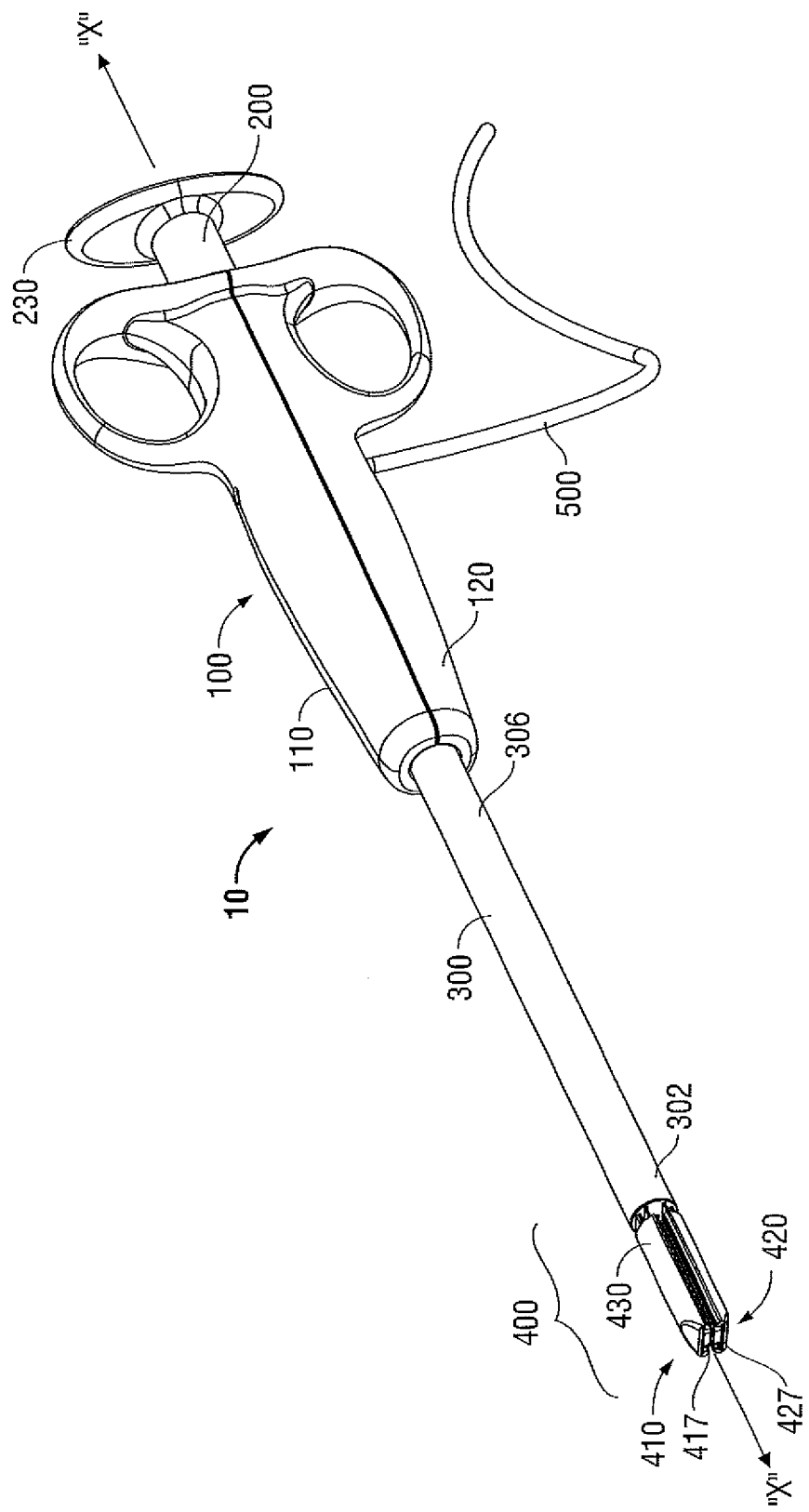
FIG. 2 is a side, perspective view of the forceps of FIG. 1, wherein the jaw members are disposed in an approximated position.

Referring now to FIGS. 1-2, a forceps is shown generally identified by reference numeral 10. Forceps 10 defines a longitudinal axis "X-X" and includes a handle assembly 100, a plunger 200 extending proximally from handle assembly 100, a shaft 300 extending distally from handle assembly 100, and an end effector assembly 400 disposed at distal end 302 of shaft 300. End effector assembly 400 includes a pair of opposed jaw members 410, 420 and a sliding unit 430 that is selectively translatable relative to jaw members 410, 420 between a proximal position (FIG. 1) and a distal position (FIG. 2) to transition jaw members 410, 420 between a spaced-apart position (FIG. 1) and an approximated position (FIG. 2) for grasping tissue therebetween. Plunger 200 is translatable relative to handle assembly 100 between an extended or proximal position (FIG. 1), wherein plunger 200 substantially extends proximally from handle assembly 100, and an inserted or distal position (FIG. 2), wherein plunger 200 is substantially disposed within handle assembly 100, in order to translate shaft 300 between proximal and distal positions relative to handle assembly 100. Translation of shaft 300 between the proximal and distal positions, in turn, effects translation of sliding unit 430 between the proximal and distal positions and, thus, transitions jaw members 410, 420 between the spaced-apart position (FIG. 1) and the approximated position (FIG. 2).

Forceps 10 also includes an electrosurgical cable 500 extending from handle assembly 100 that is electrically coupled to jaw members 410, 420 and is adapted to connect to a generator (not shown) or other suitable power source, although forceps 10 may alternatively be configured as a battery powered instrument. Cable 500 is configured to provide energy to at least one of jaw members 410, 420 of end effector assembly 400 for treating tissue grasped therebetween, as will be described in greater detail below. Although the present disclosure is described with respect to electrical energy, it is contemplated that other types of energy may also be used in conjunction with forceps 10, e.g., thermal energy, ultrasonic energy, light energy, etc.

Figure 3:
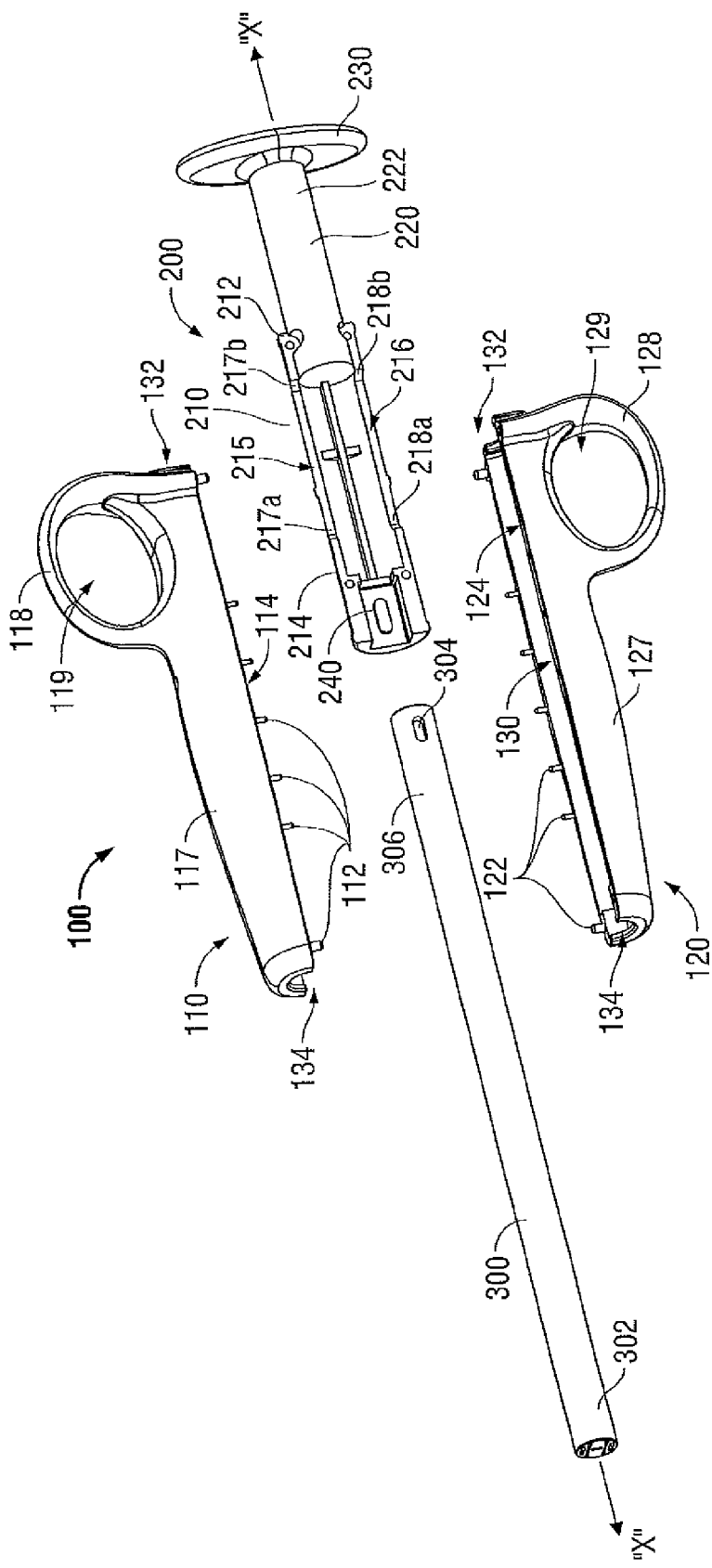
FIG. 3 is a side, perspective view of a proximal portion of the forceps of FIG. 1, shown with parts separated.
Figure 4:
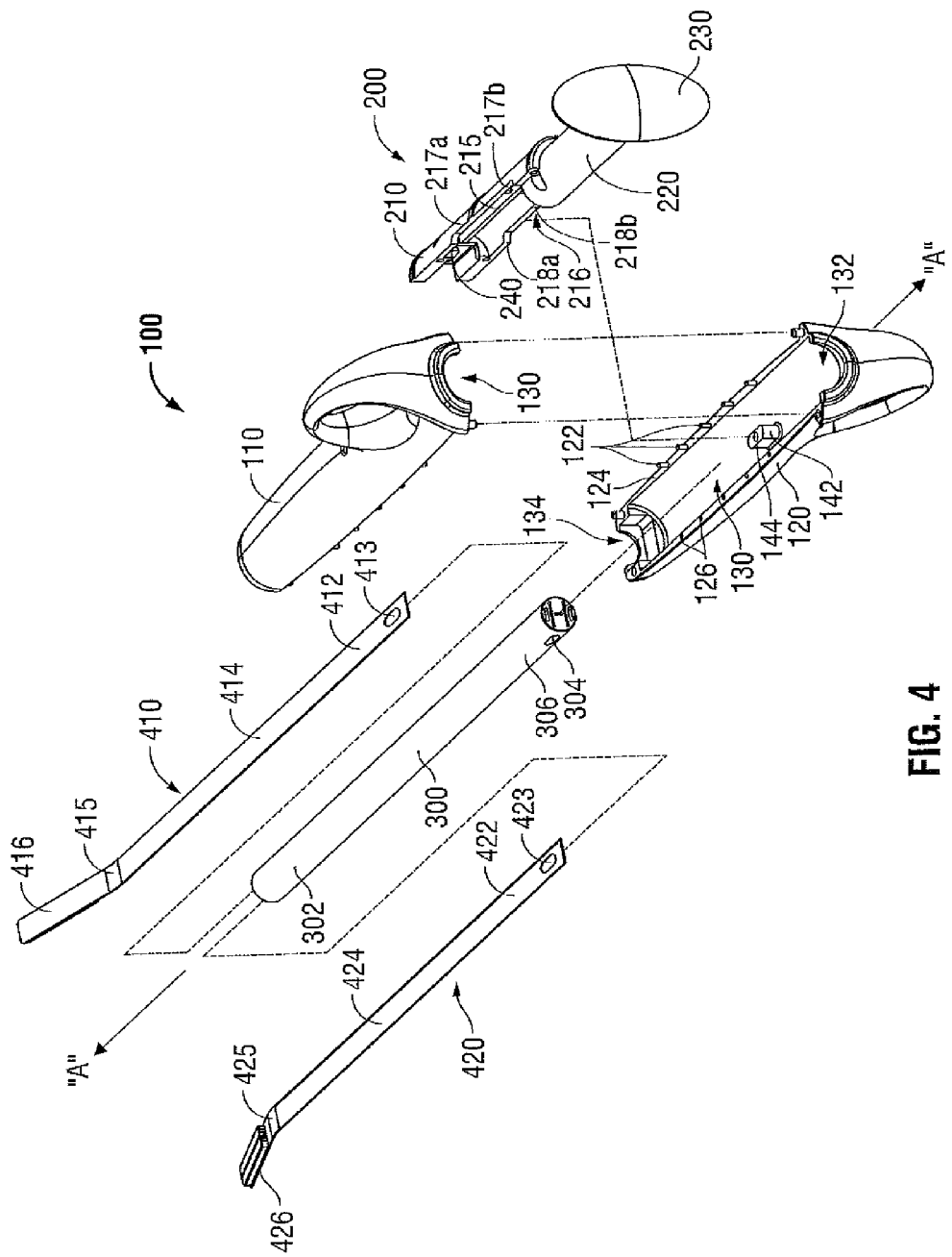
FIG. 4 is a rear, perspective view of the forceps of FIG. 1, shown with parts separated.

With reference now to FIG. 3-4, handle assembly 100 is formed from first and second housing parts 110, 120 that are engagable with one another to form handle assembly 100. More specifically, each housing part 110, 120 includes a plurality of posts 112, 122 disposed on engaging surfaces 114, 124, respectively, thereof and extending therefrom. Housing part 110 includes a plurality of apertures (not shown) defined within engaging surface 114 thereof, and housing part 120 similarly includes a plurality of apertures 126 defined within engaging surface 124 thereof. Posts 112 of housing part 110 are positioned to oppose apertures 126 of housing part 120 and, similarly, posts 122 of housing part 120 are positioned to oppose the apertures (not shown) of housing part 110 such that, upon approximation of housing parts 110, 120, posts 112 are engaged within apertures 126 and posts 122 are engaged within the apertures (not shown) defined within housing part 110 to engage first and second housing parts 110, 120, respectively, to one another.

Each housing part 110, 120 further includes an elongated body portion 117, 127 and an ergonomically-configured handle 118, 128 extending outwardly therefrom. Each handle 118, 128 defines a finger hole 119, 129 therethrough for receiving a finger of the user. As can be appreciated, finger holes 119, 129 facilitate grasping of handle assembly 100 during translation of plunger 200 relative to handle assembly 100 between the proximal and distal positions to transition jaw members 410, 420 (FIGS. 1-2) of end effector assembly 400 (FIGS. 1-2) between the spaced-apart and approximated positions.

Continuing with reference to FIGS. 3-4, body portions 117, 127 of housing parts 110, 120, respectively, cooperate with one another to define a longitudinally-extending lumen 130 therethrough. Lumen 130 is disposed about longitudinal axis "X-X" and is configured to permit reciprocation of plunger 200 through proximal portion 132 thereof, as plunger 200 is translated between the proximal and distal positions, and to permit reciprocation of shaft 300 through distal portion 134 thereof, as shaft 300 is translated between the proximal and distal positions to transition jaw members 410, 420 (FIGS. 1-2) between the spaced-apart and approximated positions. As will be described in greater detail below, plunger 200 is coupled to shaft 300 such that translation of plunger 200 along longitudinal axis "X-X" and relative to handle assembly 100 effects similar translation of shaft 300 along longitudinal axis "X-X" and relative to handle assembly 200.

Plunger 200 generally includes a distal sleeve 210, an elongated tubular member 220 extending from proximal end 212 of distal sleeve 210, and a knob 230 disposed at proximal end 222 of elongated tubular member 220. Knob 230 is configured for single handed-used, e.g., where knob 230 is grasped, or palmed, by the palm of user, while the user grasps handle assembly 100 by engagement of the user's fingers within finger holes 119, 129 of handles 118, 128, respectively, to facilitate translation of plunger 200 relative to handle assembly 100, although outer grasping configurations, e.g., two-handed operation, are also contemplated. Distal sleeve 210 may be formed from a first component 214 and a second component (not shown) substantially similar to first component 214 that, together, cooperate to define distal sleeve 210. The second component (not shown) has been removed to show the internal components of distal sleeve 210, although distal sleeve 210 may alternatively be configured with just one component 214.

Distal sleeve 210 further includes a pair of opposed slots 215, 216 defined therethrough. Slots 215, 216 are configured to receive a tab (not shown) extending inwardly from the interior surface of housing part 110 and tab 142 extending inwardly from the interior surface of housing part 120, respectively. The interior of housing part 110 is not shown; however, the interior of housing part 110 is substantially similar to that of housing part 120. Accordingly, the features and configuration of housing part 120 described and shown herein apply similarly to housing part 110, except where specifically disclaimed.

Tab 142 of housing part 120, as mentioned above, extends inwardly from the interior surface thereof and is configured to extend into slot 216 defined within distal sleeve 210. As will be described below, tab 142 of housing part 120 is configured to engage proximal end 422 of jaw member 420 thereon to retain jaw member 420 in fixed longitudinal position relative to handle assembly 100. Similarly, the tab (not shown) extending inwardly from housing part 110 is configured to engage proximal end 412 of jaw member 410 to retain jaw member 410 in fixed longitudinal position relative to handle assembly 100. More specifically, the tab (not shown) of housing part 110 and tab 142 of housing part 120 may be engaged within elongated apertures 413, 423 defined within jaw members 410, 420, respectively, towards respective proximal ends 412, 422 thereof, although any other suitable engagement mechanism may be used.

The range of translation of plunger 200 and, thus, shaft 300, relative to handle assembly 100 is defined by the length of slots 215, 216. More specifically, the proximal position of plunger 200 corresponds to the position wherein tab 142 of housing part 120 and the tab (not shown) of housing part 110 are disposed at distal ends 217a, 218a of slots 215, 216, respectively, thus inhibiting further proximal translation of plunger 200, while the distal position of plunger 200 corresponds to the position wherein tab 142 of housing part 120 and the tab (not shown) of housing part 110 are disposed at proximal ends 217b, 218b of slots 215, 216, respectively, thus inhibiting further distal translation of plunger 200.

Tab 142 of housing part 120 further includes a lumen 144 extending therethrough in transverse relation relative to longitudinal axis "X-X." Lumen 144 extends from tab 142 completely through housing part 120 and is configured to receive cable 500 (FIGS. 1-2) therethrough. More specifically, cable 500 extends through lumen 144 of housing part 120 into handle assembly 100, ultimately electrically coupling to proximal end 422 of jaw member 420 (and/or proximal end 412 of jaw member 410), which is engaged to tab 142 of housing part 120. As such, energy may be supplied from an energy source (not shown) via cable 500 to jaw member 410. Additionally, or alternatively, a lumen (not shown) may be defined within the tab (not shown) of housing part 110 to permit passage of a cable (not shown) therethrough for coupling jaw member 410 to the energy source (not shown).

With continued reference to FIGS. 3-4, and as mentioned above, plunger 200 is coupled to shaft 300 such that translation of plunger 200 along longitudinal axis "X-X" effects similar translation of shaft 300 along longitudinal axis "X-X."

More specifically, shaft 300 includes a pair of recesses 304 defined within opposed lateral sides of shaft 300 at proximal end 306 thereof that are configured to receive protrusions 240 extending inwardly from distal sleeve 210 of plunger 200 to engage plunger 200 and shaft 300 to one another on either side of shaft 300. Alternatively, plunger 200 and shaft 300 may be formed monolithically as a single component that includes slots 215, 216 defined therethrough to permit engagement of jaw members 410, 420 and handle assembly 100 to one another.

Figure 5:
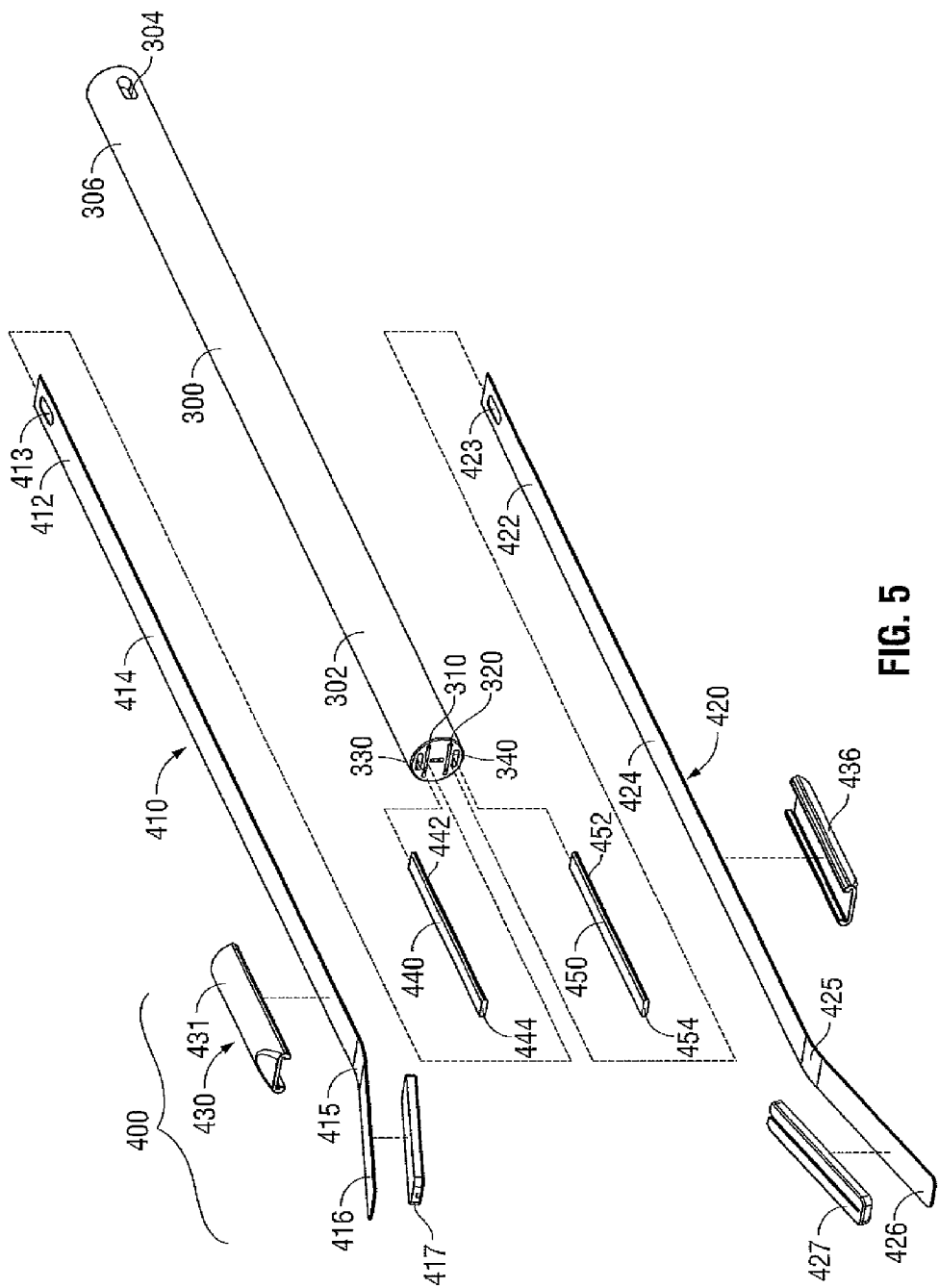
FIG. 5 is a front, perspective view of a shaft assembly of the forceps of FIG. 1, shown with parts separated.
Figure 6:
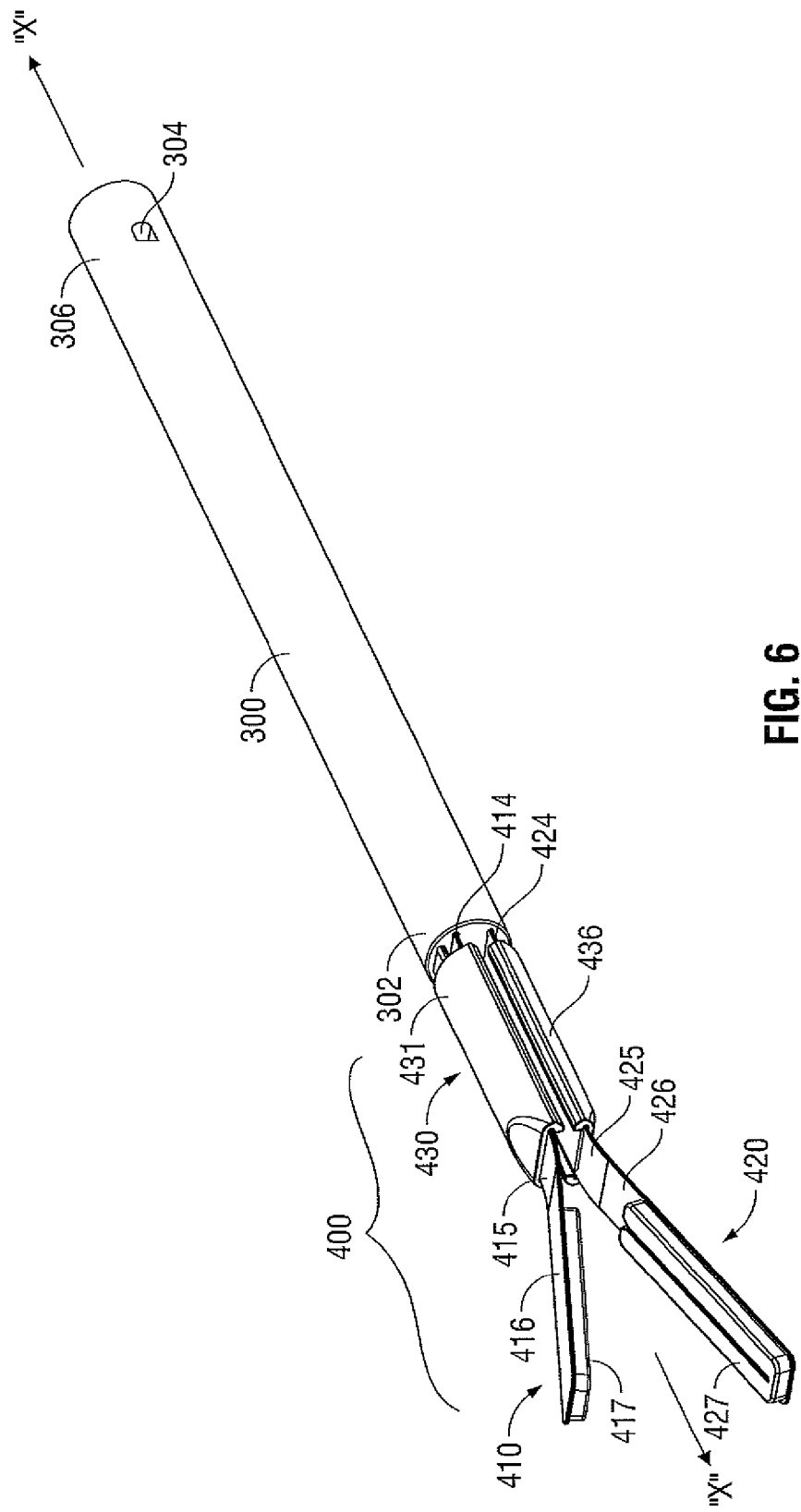
FIG. 6 is a front, perspective view of a distal end of the forceps of FIG. 1.
Figure 7:
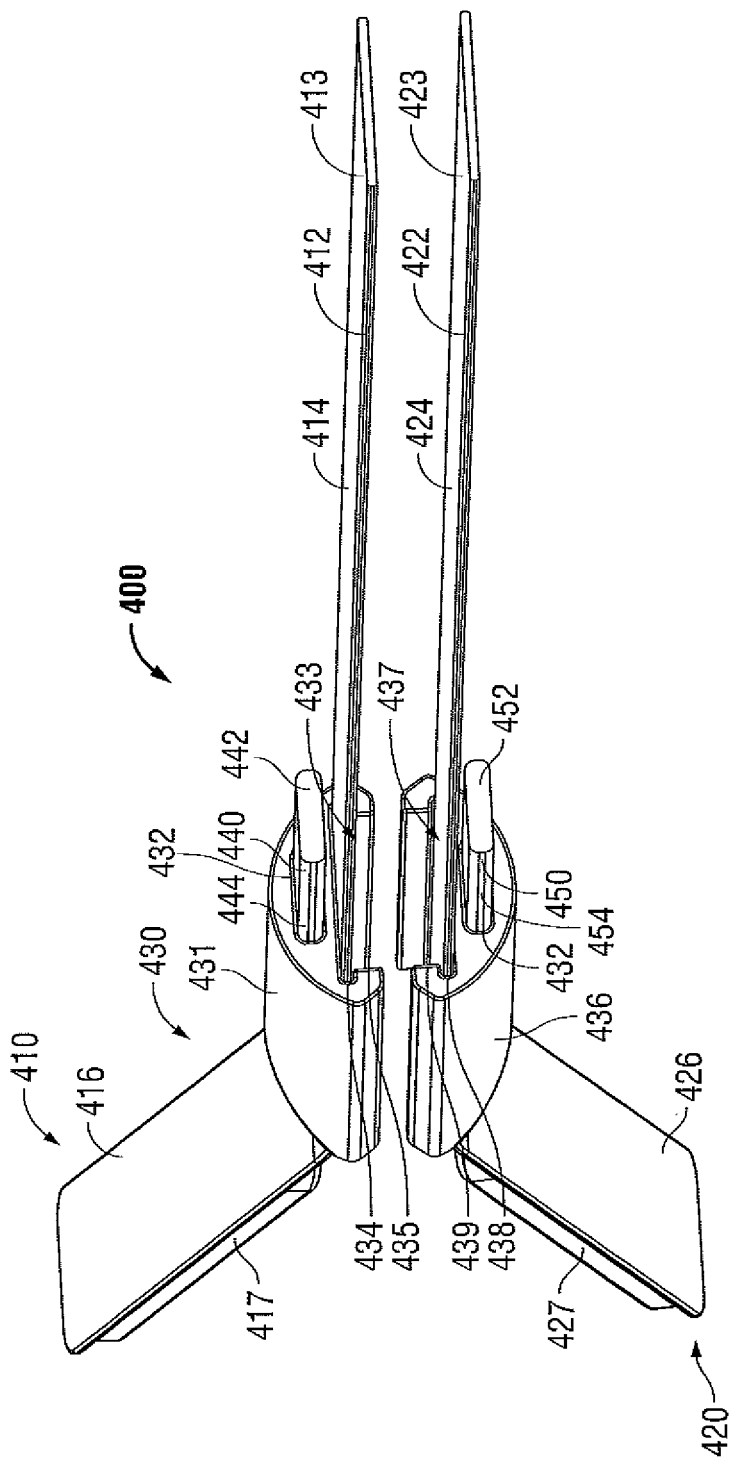
FIG. 7 is a rear, perspective view of an end effector assembly of the forceps of FIG. 1.

Turning now to FIGS. 5-7, shaft 300 and end effector assembly 400 are shown. Shaft 300 defines an elongated, generally cylindrical configuration having a distal end 302 and a proximal end 306 and defining a plurality of lumens extending at least partially therethrough. First and second opposed lumens 310, 320 are symmetrically disposed on either side of longitudinal axis "X-X" and extend completely through shaft 300. First and second lumens 310, 320 are configured to receive proximal portions 414, 424 of jaw members 410, 420, respectively, therethrough. Lumens 310, 320 are configured such that shaft 300 is selectively translatable relative to jaw members 410, 420 between the proximal and distal positions, i.e., such that jaw members 410, 420 are translatable through lumens 310, 320, respectively, of shaft 300.

Third and fourth opposed lumens 330, 340 are symmetrically disposed on either side of longitudinal axis "X-X" and are positioned farther-apart from one another as compared to first and second lumens 310, 320, i.e., lumens 330, 340 are defined towards the outer periphery of shaft 300, while first and second lumens 310, 320, are more-inwardly disposed. Third and fourth lumens 330, 340 extend partially through shaft 300 from distal end 302 thereof and are configured to engage proximal ends 442, 452 of support bars 440, 450, respectively, of end effector assembly 400 therein, e.g., in friction-fit engagement therewith. Distal ends 444, 454 of support bars 440, 450, on the other hand, are configured for engagement within lumens 432 defined within first and second components 431, 436 of sliding unit 430. As such, shaft 300 and sliding unit 430 of end effector assembly 400 are engaged to one another via support bars 440, 450 such that translation of shaft 300 effects similar translation of sliding unit 430.

With continued reference to FIGS. 5-7, sliding unit 430 is formed from an electrically-insulative material and includes first and second components 431, 436, respectively, that each define opposed, hemispherical configurations, although other configurations are contemplated. First and second components 431, 436 of sliding unit 430, as mentioned above, engage distal ends 444, 454 of support bars 440, 450, respectively, within lumens 432 thereof. First and second components 431, 436 of sliding unit 430 each further include a track 433, 437, respectively, defined longitudinally therethrough. Tracks 433, 437, in turn, each include a first track section 434, 438, configured to receive jaw members 410, 420, respectively, therethrough, and a second track section 435, 439, configured to receive sealing plates 417, 427, respectively, therethrough upon translation of sliding unit 430 to the distal position to approximate jaw members 410, 420.

Jaw members 410, 420 of end effector assembly 400 each define an elongated, generally flat, rectangular configuration permitting jaw members 410, 420 to extend completely through shaft 300 and into engagement with handle assembly 100 (FIGS. 1-2). More specifically, jaw members 410, 420 each include a proximal segment 414, 424 that extends through shaft 300 and into handle assembly 100 (FIGS. 1-2), a flexible intermediate segment 415, 425, and a distal segment 416, 426, respectively, that retains sealing plates 417, 427, respectively, thereon. Further, jaw members 410, 420 are formed at least partially from an electrically-conductive material such that energy supplied by cable 500 (FIGS. 1-2) may be transmitted from proximal ends 412, 422 of proximal segments 414, 424, respectively, thereof, to distal segments 416, 426, respectively, thereof. In other words, jaw members 410, 420 may be configured as electrodes 410, 420, respectively.

Continuing with reference to FIGS. 5-7, flexible intermediate segments 415, 425, of jaw members 410, 420 (or the entirety of jaw members 410, 420) are formed as flat-springs (or any other suitable biasing members) that are biased-apart from one another such that, as shown in FIG. 6, jaw members 410, 420 are disposed in the spaced-apart position when sliding component 430 is disposed in the proximal position. As will be described below, as sliding component 430 is translated distally along longitudinal axis "X-X" and relative to jaw members 410, 420, jaw members 410, 420 are brought into approximation with one another, against the bias of intermediate segments 415, 425, due to the increasing engagement of jaw members 410, 420 within first track sections 434, 438 of tracks 433, 437, respectively, of sliding component 430.

Figure 8A:
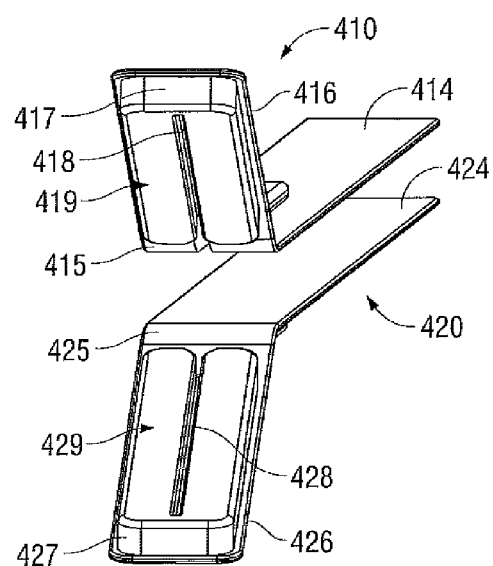
FIG. 8A is a front, perspective view of the jaw members of the forceps of FIG. 1.
Figure 8B:
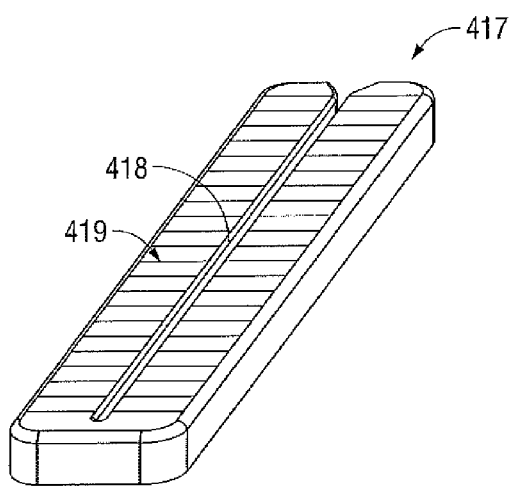
FIG. 8B is an enlarged, front, perspective view of one of the jaw members of the forceps of FIG. 1.
Figure 8C:
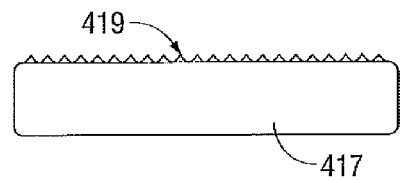
FIG. 8C is a side view of the jaw member of FIG. 8B.

Referring now to FIGS. 8A-8C, in conjunction with FIGS. 5-7, jaw members 410, 420 each include an electrically-conductive tissue sealing plate 417, 427, respectively, disposed thereon in opposed relation relative to one another. Tissue sealing plates 417, 427 may be engaged on distal segments 416, 426 of jaw members 410, 420, respectively, in any suitable fashion, e.g., welding, adhesion, etc., or may be monolithically formed therewith. Tissue sealing plates 417, 427 are configured to grasp tissue therebetween upon approximation of jaw members 410, 420 and are electrically coupled to jaw members 410, 420 such that energy may be conducted between tissue sealing plates 417, 427 and through tissue grasped therebetween to effect a tissue seal. For example, the electrically-conductive tissue sealing plates 417, 427 may be disposed in contact with respective electrically-conductive jaw members 410, 420 such that electrical energy may be transmitted therebetween, although any other suitable electrical connection may also be provided. Further, jaw member 410 and/or jaw member 420 may also include a longitudinally-extending knife channel 418, 428, respectively, defined therethrough that is configured to permit reciprocation of a knife 700 (FIGS. 10A-10B) therethrough to cut tissue grasped between jaw members 410, 420, e.g., to cut sealed tissue along the tissue seal.

Tissue sealing plates 417, 427 of jaw members 410, 420, respectively, as shown in FIGS. 5-8C, may also include textured tissue-grasping surfaces 419, 429, respectively, to facilitate the grasping and retention of tissue therebetween as jaw members 410, 420 are moved from the spaced-apart position to the approximated position. More specifically, tissue sealing plates 417, 427 of jaw members 410, 420, respectively, may include serrations, protrusions, or other suitable surface features defined on tissue-grasping surfaces 419, 429, respectively, thereof, that are configured to facilitate the grasping and retention of tissue therebetween without damaging tissue.

Figure 9:
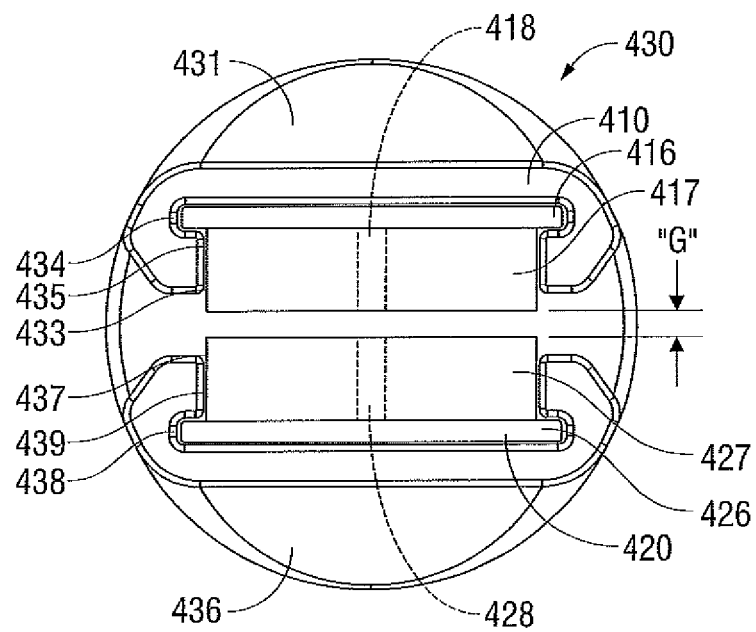
FIG. 9 is a front view of the end effector assembly of the forceps of FIG. 1.

Turning to FIG. 9, end effector assembly 400 is shown wherein sliding unit 430 is disposed in the distal position substantially surrounding distal segments 416, 426 of respective jaw members 410, 420 such that jaw members 410, 420 are disposed in the approximated position. More specifically, in this position, jaw members 410, 420 are disposed within first track sections 434, 438, of first and second components 431, 436, respectively, of sliding unit 430, while sealing plates 417, 427 are disposed within second track section 435, 439 of first and second components 431, 436, respectively, of sliding unit 430. Further, in this position, tissue sealing plates 417, 427 extend from respective components 431, 436 of sliding unit 430 toward one another to define a minimum gap distance "G" therebetween. The engagement of jaw members 410, 420 within first track sections 434, 438 of tracks 433, 437, respectively, inhibits further approximation of jaw members 410, 420 relative to one another, thus maintaining this minimum gap distance "G" therebetween. Gap distances "G" in the range of about 0.001 inches to about 0.006 inches are contemplated, although sliding unit 430 may be configured to achieve other suitable gap distances "G."

Figure 10A:
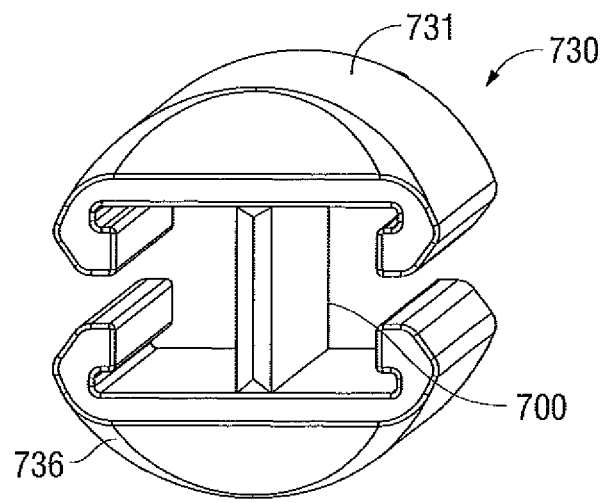
FIG. 10A is a front, perspective view of another embodiment of an end effector assembly provided in accordance with the present disclosure and configured for use with the forceps of FIG. 1.
Figure 10B:
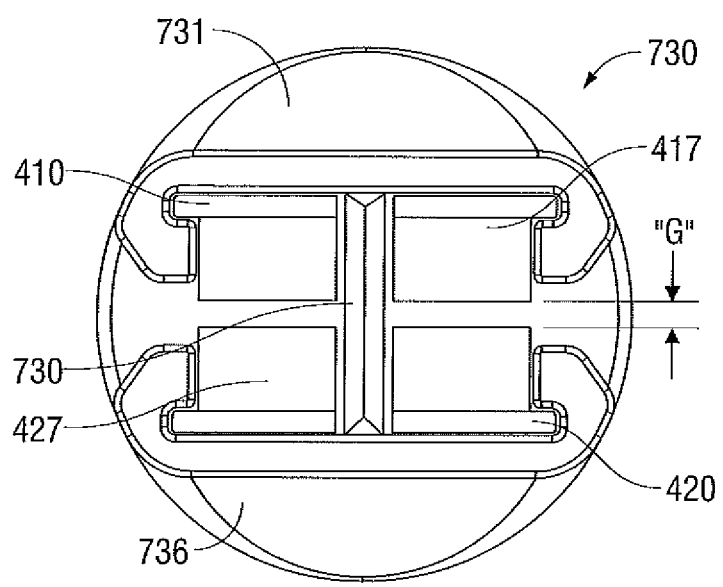
FIG. 10B is a front view of the end effector assembly of FIG. 10A shown including a pair of jaw members disposed therein.

With reference to FIGS. 10A-10B, another embodiment of a sliding unit 730 is shown. Sliding unit 730 is substantially similar to sliding unit 430 (FIGS. 1-2) except that sliding unit 730 includes a knife 700 disposed therein and extending between first and second components 731, 736, respectively, of sliding unit 730. Thus, as sliding unit 730 is translated distally from the proximal position to the distal position to approximate jaw members 410, 420 to grasp tissue therebetween, knife 700 is simultaneously advanced distally through knife channels 418, 428 defined within tissue sealing plates 417, 427 of jaw members 410, 420, respectively, to cut tissue grasped therebetween. Such a configuration permits simultaneous, or near-simultaneous, grasping, sealing, and cutting of tissue (or only grasping and cutting of tissue, depending on a particular purpose). Alternatively, knife 700 may be configured for selectively translation, independent of sliding unit 730, to cut tissue grasped between jaw members 410, 420.

Referring to FIGS. 1-2, in conjunction with FIGS. 3-9, the use and operation of forceps 10 is described. Initially, as shown in FIG. 1, plunger 200 is disposed in the proximal position, wherein plunger 200 extends proximally from handle assembly 100. With plunger 200 in this proximal position, shaft 300 and sliding unit 430 are likewise disposed in their respective proximal positions such that jaw members 410, 420 of end effector assembly 400 extend distally from sliding unit 430 and are disposed in the spaced-apart position under the bias of intermediate segments 415, 425, respectively. With forceps 10 disposed in this position, forceps 10 may be maneuvered and/or manipulated into position within a surgical site such that tissue to be grasped, sealed, and/or divided is disposed between tissue sealing plates 417, 427 of jaw members 410, 420, respectively.

With tissue disposed between jaw members 410, 420 of end effector assembly 400, jaw members 410, 420 may be transitioned to the approximated position to grasp tissue therebetween. More specifically, in order to transition jaw members 410, 420 from the spaced-apart position, to the approximated position, the user grasps handles 118, 128 of handle assembly 100 with the user's hand, e.g., via inserting one or more fingers through each of finger holes 119, 129, and palms, or grasps knob 230 of plunger 200 with the palm of the same hand (or the thumb thereof). Alternatively, the user may grasp handles 118, 128 with one hand, while grasping knob 230 with other hand. Other suitable configurations may also be used, depending on the user's preference.

While grasping both handle assembly 100 and plunger 200, the user translates knob 230 distally relative to handle assembly 100, thereby translating plunger 200 from the proximal position to the distal position, wherein plunger 200 is substantially disposed within handle assembly 100. As mentioned above, translation of plunger 200 to the distal position effects similar translation of shaft 300 and sliding unit 430 distally. The engagement of jaw members 410, 420 within handle assembly 100 maintains jaw members 410, 420 in fixed longitudinal position relative to handle assembly 100 such that plunger 200, shaft 300, and sliding unit 430 are not only translated distally relative to handle assembly 100, but are also translated distally relative to jaw members 410, 420 of end effector assembly 400.

As sliding unit 430 is translated distally relative to jaw members 410, 420, jaw members 410, 420 and tissue sealing plates 417, 427 are translated into and through first and second track sections 434, 438 and 435, 439, respectively, of first and second components 431, 436, respectively, of sliding unit 430, such that jaw members 410, 420 are brought into approximation with one another to grasp tissue therebetween. As mentioned above, the surface feature(s) of tissue sealing plates 417, 427 may facilitate the grasping of tissue therebetween as jaw members 410, 420 are flexed from the biased, spaced-apart position, towards the approximated position. After, or simultaneously with, the grasping of tissue between tissue sealing plates 417, 427 of jaw members 410, 420, respectively, energy may be supplied to one or both of tissue sealing plates 417, 427 of jaw members 410, 420, respectively, e.g., via cable 500, to seal tissue grasped therebetween. The creation of an effective tissue seal is facilitated by the maintenance of the minimum gap distance "G" (FIG. 9) between tissue sealing plates 417, 427 when jaw members 410, 420 are disposed in the approximated position. Further, the insulative sliding unit 430, which is disposed about jaw members 410, 420 and tissue sealing plates 417, 427 when in the distal position, inhibits thermal damage to surrounding tissue as the tissue sealing plates 417, 427 are energized during tissue sealing.

Referring to FIGS. 10A-10B, in embodiments where knife 700 is disposed within the sliding unit 730, tissue is cut, or divided simultaneously, or near simultaneously with the grasping and sealing of tissue. More specifically, as sliding unit 730 is advanced over jaw members 410, 420 to transition jaw members 410, 420 to the approximated position, energy is supplied to one or both of tissue sealing plates 417, 427 of jaw members 410, 420, respectively, e.g., via cable 500, to seal tissue grasped therebetween, while knife 700 is advanced through knife channels 418, 428 of jaw members 410, 420, respectively, to cut tissue along the tissue seal. However, sealing of tissue need not necessarily be performed, as sliding unit 730 may simply be advanced over jaw members 410, 420 to grasp and divide tissue disposed therebetween.

At the completion of grasping, sealing and/or cutting operation, knob 230 of plunger 200 may be translated proximally relative to handle assembly 100 back to the proximal position such that shaft 300 and sliding unit 430 are returned back to their respective proximal positions, thus allowing jaw members 410, 420 to return, under the bias of intermediate segments 415, 425, respectively, back to the spaced-apart position to release the sealed and/or divided tissue. Finally, forceps 10 may be removed from the surgical site.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly, including:
first and second jaw members, each jaw member including an elongated proximal segment and a distal segment, the distal segments biased towards a spaced-apart position relative to one another;
first and second tissue sealing plates disposed on the distal segments of the first and second jaw members, respectively; and
a sliding unit disposed about the first and second jaw members, the sliding unit including first and second tracks, each of the first and second tracks including a first portion complementary to the first and second jaw members, respectively, and a second portion, separate from the first portion, complementary to the first and second tissue sealing plates, respectively, the sliding unit slidable relative to the jaw members between a first position, wherein the sliding unit is disposed about a portion of each of the elongated proximal segments of the jaw members with a portion of each of the elongated proximal segments disposed within the first portion of the respective track, and a second position, wherein the sliding unit is disposed about at least a portion of each of the distal segments of the jaw members with at least a portion of each of the distal segments disposed within the first portion of the respective track and at least a portion of each of the tissue sealing plates disposed within the second portion of the respective track, the sliding unit configured to transition the distal segments against the bias from the spaced-apart position to an approximated position for grasping tissue between the first and second tissue sealing plates upon sliding of the sliding unit from the first position to the second position.

2. The forceps according to claim 1, further comprising a plunger coupled to the sliding unit and configured for movement relative to the jaw members between a proximal position and a distal position for sliding the sliding unit between the first and second positions.

3. The forceps according to claim 2, wherein the plunger further includes a knob disposed at a proximal end thereof and configured to facilitate translation of the plunger between the proximal and distal positions.

4. The forceps according to claim 2, further comprising a housing, the first and second jaw members engaged to the housing at proximal ends thereof.

5. The forceps according to claim 4, wherein the housing includes first and second handles extending outwardly therefrom, the handles configured to facilitate grasping of the housing.

6. The forceps according to claim 4, wherein the plunger is selectively translatable relative to the housing between the proximal position, wherein the plunger substantially extends proximally from the housing, and the distal position, wherein the plunger is substantially disposed within the housing.

7. The forceps according to claim 4, further comprising a shaft extending distally from the housing, the shaft engaged to the plunger at a proximal end thereof such that movement of the plunger between proximal and distal positions effects similar movement of the shaft between a proximal position and a distal position, the shaft engaged to the sliding unit at a distal end thereof such that movement of the shaft between the proximal and distal positions slides the sliding unit relative to the jaw members between the first and second positions.

8. The forceps according to claim 7, wherein the proximal segment of each of the jaw members extends proximally through a lumen defined within the shaft and into the housing, the proximal segments of the jaw members engaged within the housing at the proximal ends thereof.

9. The forceps according to claim 1, wherein the tissue sealing plates are formed from an electrically-conductive material and are adapted to conduct electrical energy therebetween for sealing tissue grasped therebetween.

10. The forceps according to claim 9, wherein the jaw members are formed from an electrically-conductive material to transmit electrosurgical energy from a proximal end thereof to the tissue sealing plates disposed thereon.

11. The forceps according to claim 1, wherein the sliding unit is formed from an insulative material.

12. The forceps according to claim 1, further comprising a knife engaged within the sliding unit, the knife configured to cut tissue grasped between the jaw members upon sliding of the sliding unit from the first position to the second position.

13. The forceps according to claim 12, wherein at least one of the jaw members includes a knife channel extending longitudinally therethrough, the knife channel configured to permit reciprocation of the knife therethrough as the sliding unit is slid between the first and second positions.

14. The forceps according to claim 1, wherein each of the jaw members further includes an intermediate segment interconnecting the proximal and distal segments thereof, the intermediate segment of at least one of the jaw members including a biasing member configured to bias the jaw members towards the spaced-apart position.

15. The forceps according to claim 14, wherein the intermediate segment of the at least one jaw members includes a flat spring.

16. A forceps, comprising:
a housing;
a plunger coupled to the housing and configured for longitudinal translation relative to the housing between an extended position, wherein the plunger substantially extends proximally from the housing, and an inserted position, wherein the plunger is substantially disposed within the housing;
a shaft extending distally from the housing, the shaft engaged to the plunger such that movement of the plunger between the extended and inserted positions effects similar movement of the shaft between a proximal position and a distal position; and
an end effector assembly disposed at a distal end of the shaft, the end effector assembly including:
first and second jaw members, each jaw member including an elongated proximal segment engaged to the housing and extending distally through a lumen defined through the shaft, each jaw member including a distal segment extending distally from the elongated proximal segment, the distal segments biased towards a spaced-apart position relative to one another;
first and second tissue sealing plates disposed on the distal segments of the first and second jaw members, respectively; and
a sliding unit disposed about the first and second jaw members, the sliding unit including first and second tracks, each of the first and second tracks including a first portion complementary to the first and second jaw members, respectively, and a second portion, separate from the first portion, complementary to the first and second tissue sealing plates, respectively, the sliding unit slidable relative to the jaw members between a first position, wherein the sliding unit is disposed about a portion of each of the elongated proximal segments of the jaw members with a portion of each of the elongated proximal segments disposed within the first portion of the respective track, and a second position, wherein the sliding unit is disposed about at least a portion of each of the distal segments of the jaw members with at least a portion of each of the distal segments disposed within the first portion of the respective track and at least a portion of each of the tissue sealing plates disposed within the second portion of the respective track, the sliding unit configured to transition the distal segments against the bias from the spaced-apart position to an approximated position for grasping tissue between the first and second tissue sealing plates upon sliding of the sliding unit from the first position to the second position.

\* \* \* \* \*